United States Patent [19]

McEwen

[11] Patent Number: 5,048,536
[45] Date of Patent: Sep. 17, 1991

[54] TOURNIQUET FOR REGULATING APPLIED PRESSURES

[76] Inventor: James A. McEwen, 10551 Bamberton Drive, Richmond, British Columbia, Canada, V7A 1K6

[21] Appl. No.: 388,699

[22] Filed: Jul. 13, 1989

Related U.S. Application Data

[63] Continuation-in-part of Ser. No. 33,770, Apr. 3, 1987, Pat. No. 4,869,265.

[51] Int. Cl.$^5$ ............................................. A61B 5/00
[52] U.S. Cl. ................................... 128/748; 128/774; 606/203
[58] Field of Search ................ 128/686, 748, 774–782; 606/203, 202, 201; 200/83 N, 83 Y, 81.4, 211, 212, 214

[56] References Cited

U.S. PATENT DOCUMENTS

| | | | |
|---|---|---|---|
| 3,095,873 | 7/1963 | Edmunds | 128/205 |
| 3,958,562 | 5/1976 | Hakim et al. | 128/748 |
| 4,114,603 | 9/1978 | Wilkinson | 128/748 |
| 4,147,161 | 4/1979 | Ikabe et al. | 128/748 |
| 4,299,230 | 11/1989 | Kubok | 128/748 |
| 4,378,809 | 4/1983 | Cosman | 128/748 |
| 4,385,636 | 5/1983 | Cosman | 128/748 |
| 4,469,099 | 9/1984 | McEwen | 128/327 |
| 4,476,871 | 10/1984 | Hon | 128/775 |
| 4,479,494 | 10/1984 | McEwen | 128/327 |
| 4,549,550 | 10/1985 | Kami | 606/203 |
| 4,605,010 | 8/1986 | McEwen | 128/686 |
| 4,770,175 | 9/1988 | McEwen | 128/327 |

FOREIGN PATENT DOCUMENTS

1082429 3/1984 U.S.S.R. ............... 128/774

OTHER PUBLICATIONS

J. A. McEwen and R. W. McGraw, "An Adaptive Tourniquet for Improved Safety in Surgery", IEEE Trans. Bio-Med Eng., vol. BME 29, 1982, pp. 122–128.
J. A. McEwen and G. F. Auchinleck, "Advances in Surgical Tourniquets," J.A.O.R.N., vol. 36, 1982, pp. 889–896.
J. A. Shaw and D. G. Murray, "The Relationship Between Tourniquet Pressure and . . ." J. Bone & Joint Surg., vol. 64-A, Oct. 1982, pp. 1148–1152.
A. C. McLaren and C. H. Rorabeck, "The Pressure Distribution Under Tourniquets", J. Bone & Joint Surg., 67A, Mar. 1985, pp. 433–438.
R. J. Newman and A. Muirhead, "A Safe & Effective Low Press Tourniquet", J. Bone & Joint. Surg., 68B, Aug. 1986, p. 625–628.
J. A. Shaw et al., "Guidelines for the Use of Digital Tourniquets. . . " J. Bone & Joint Surg., 67A, Sep. 1985, pp. 1086–1090.
S. E. Grice et al., "Intravenous Regional Anesthesia: Evaluation and Prevention of Leakage. . . " Anesthesiology, 65, pp. 316∝320, Sep. 1986.

*Primary Examiner*—Max Hindenburg

[57] ABSTRACT

A tourniquet comprising: (a) an occlusive band for encircling a limb of a subject and for applying pressure to the limb wherein an inner surface of at the band faces the limb; and applied pressure sensing means located at a predetermined position on the inner surface of the band for producing an indication of the pressure applied by the band to the limb near the predetermined location. The applied pressure sensing means is comprised of material having a degree of flexibility and physical dimensions selected so that the sensing means conforms closely to the surface of the occlusive band and does not substantially displace the surface of the limb away from the band surface. The applied pressure sensing means produces an applied pressure signal representative of the pressure applied by the band to the limb near the predetermined location, the occlusive band is responsive to a varible pressure control signal, and pressure-regulating means responsive to the applied pressure signal is included for producing a pressure control signal to maintain the pressure applied by the band to the limb near a predetermined reference pressure.

11 Claims, 6 Drawing Sheets ns. For example,
completely detached from a limb, and thus completely ineffective,
TOURNIQUET FOR REGULATING APPLIED PRESSURES

REFERENCE TO RELATED APPLICATION

This is a continuation of U.S. Pat. Application Ser. No. 07/033,770, filed Apr. 3, 1987, U.S. Pat. No. 4,869,265 issued 09/26/89.

FIELD OF THE INVENTION

This invention pertains to medical devices which apply controlled pressures to tissues, organs or limbs of living bodies near predetermined locations relative to the devices. The invention particularly pertains to a tourniquet useful in surgery for controlling and occluding blood flow into a portion of a limb, comprising: an occlusive band for encircling a limb of a subject and for applying pressure to the limb, wherein an inner surface of the band faces the limb; and applied pressure sensing means located at a predetermined position on the inner surface of the band for producing an indication of the pressure applied by the band to the limb near the predetermined location. Pressure-regulating means may be included to maintain the pressure applied at the predetermined location near a predetermined reference pressure.

BACKGROUND OF THE INVENTION

Surgical tourniquet systems are widely used to facilitate surgical procedures on portions of arms or legs of patients by occluding blood flow into those limb portions for periods ranging from a few minutes to several hours.

A surgical tourniquet system at present typically includes an inflatable cuff for encircling the limb and for applying pressure to the encircled limb, pressure regulating means intended for maintaining the pressure applied by the cuff near a desired pressure, and means for setting the desired pressure, either at a constant level or at a level which varies in response to a changing physiological parameter such as systolic mean or diastolic blood pressure.

In principle, it is considered safest to maintain the cuff pressure near the "minimum effective pressure", i.e. the lowest pressure that will occlude blood flow past the cuff. In practice, the minimum effective pressure is difficult to predict and achieve because it is a function of many variables, including the patient's changing blood pressure, the patient's limb size and tissue characteristics, the relative match of cuff shape to limb shape, cuff characteristics such as its width, and the technique of cuff application to the limb.

A related safety issue concerns the pressure distribution or pressure gradient generated beneath an encircling cuff. The results of tests performed on animals, cadavers and to some extent humans, as described in the cited prior art, clearly indicate that high gradients of pressure applied to nerve tissues beneath tourniquet cuffs are associated with higher probabilities of nerve injury. Conversely, lower pressure gradients are associated with lower probabilities of nerve injury. These findings would appear to have important implications for surgical tourniquet systems, but surprisingly no tourniquet system known to the applicant in the prior art permits the estimation and regulation of the pressure actually applied by the cuff to the limb near one or more predetermined locations relative to the cuff.

At present, all commercially available tourniquet systems employ pneumatic cuffs and pneumatic pressure regulating mechanisms. These systems monitor and maintain the pressure in an inflatable bladder in the cuff, but do not estimate the pressure actually applied by the cuff to the limb at the cuff/limb interface. For example, in the extreme, one could envision a cuff completely detached from a limb, and thus completely ineffective, in which the bladder pressure continues to be maintained precisely near a desired level.

Recently, research and clinical investigations were performed using a tourniquet cuff incorporating a novel biomedical pressure transducer, described in my copending United States patent application having serial number 07/033,770 and filed Apr. 3, 1987. This application having serial number 07/033,770 is herein incorporated by reference. The clinical investigations performed using the novel biomedical pressure transducer have revealed many significant discrepancies between the pressure maintained in the inflatable chamber of a pneumatic tourniquet cuff and the pressure actually applied by the cuff to the encircled limb. For example, with the transducer oriented to estimate applied pressure near a plurality of predetermined cuff locations in an axial direction from the proximal to the distal edge of the cuff, it was found that the pressure varied from a level of almost zero near the edges to a maximum level near the cuff center, and it was found that the maximum level differed significantly from the pressure in the cuff bladder as a function primarily of how snugly the cuff had been wrapped around the limb. Normal variations in snugness were found to vary the maximum pressure actually applied to the limb by 50 percent or more in comparison to the regulated bladder pressure; such a discrepancy is undesirable clinically, and in many clinical situations, such as in the use of intravenous regional anesthesia, such a discrepancy can present a life-threatening hazard.

Further tests with a tourniquet cuff including the above-referenced biomedical pressure transducer have revealed significant pressure variations in the pressure applied to a limb in a circumferential direction around the limb, particularly in the region where the cuff overlaps itself as it encircles the limb. Such variations can be hazardous.

Tests of a variety of pneumatic tourniquet cuffs and non-pneumatic occlusive bands which have included the above referenced transducer but which have had different designs, as well as tests of each such cuff on a variety of limb shapes, have shown that a wide variety of pressure gradients can be applied to the encircled limb and to the underlying nerve tissues.

No surgical tourniquet system in the prior art known to the applicant accurately estimates the level of pressure actually applied to the limb near a predetermined cuff location, when the specific cuff of that system is applied with an arbitrary degree of snugness to a limb of arbitrary shape. Moreover, the applicant is unaware of any surgical tourniquet system known in the prior art which can accurately estimate the axial pressure distribution, the circumferential pressure distribution, or the maximum pressure actually applied to the limb in view of the above described variables. Finally, and accordingly, no tourniquet system is known in the prior art which can regulate the maximum pressure actually applied by the cuff to the limb which it encircles, or the pressure applied near one cuff location, or the pressures actually applied to the limb near multiple cuff locations in relation to desired pressure levels.

An object of the present invention is to provide a tourniquet which is capable of indicating a pressure actually applied by a cuff to a limb near any predetermined location beneath the cuff, in a manner which continues to be accurate despite differences in the initial snugness of cuff application on different limbs, and despite considerable intra-operative changes in the degree of snugness and shape match between the cuff and limb as a result of limb manipulation in surgery, for example. A related object of the invention is to provide a tourniquet capable of accurately regulating a pressure actually applied by a cuff to a limb near a predetermined location relative to the cuff.

A further object of the present invention is to provide a tourniquet capable of indicating multiple pressures actually applied by a cuff to a limb near multiple predetermined locations beneath the cuff. A related object is to provide a tourniquet capable of producing a clinically desired distribution or gradient of pressures on the limb beneath the cuff by, for example, making changes in the design of the cuff which change the applied pressures appropriately. Another related object of the invention is to provide a tourniquet which is capable of separately regulating the pressures applied by the cuff to the limb near multiple predetermined locations beneath the cuff, so that clinically desired distributions or gradients of pressures in circumferential and axial directions can be maintained for an extended period of time. A further related object is to provide a tourniquet in which the distribution or gradient of pressures applied by the cuff to the limb can be conveniently specified and changed from time to time by a clinical operator of the tourniquet.

The applicant is aware of the following United States patents which are more or less relevant to the subject matter of the applicant's invention.

| | | | | |
|---|---|---|---|---|
| 4,770,175 | 9/1988 | McEwen | | 128/327 |
| 4,605,010 | 8/1986 | McEwen | | 128/686 |
| 4,479,494 | 10/1984 | McEwen | 128/327 | 128/682 |
| 4,469,099 | 9/1984 | McEwen | 128/327 | 128/682 |

The applicant is also aware of the following published references which are more or less relevant to the subject matter of the applicant's invention.

J. A. McEwen and R. W. McGraw, "An adaptive tourniquet for improved safety in surgery." IEEE Transactions in Biomedical Engineering, Vol.BME-29, February 1982, pp. 122-128.

J. A. McEwen and G. F. Auchinleck, "Advances in surgical tourniquets." J. Assn. Operating Room Nurses, Vol. 36, 1982, pp. 889-896.

J. A. Shaw and D. G. Murray, "The relationship between tourniquet pressure and underlying soft-tissue pressure in the thigh." The Journal of Bone and Joint Surgery, Vol. 64-A, 1982, pp. 1148-1152.

A. C. McLaren and C. H. Rorabeck, "The pressure distribution under tourniquets." The Journal of Bone and Joint Surgery, Vol. 67-A, 1985, pp. 433-438.

R. J. Newman and A. Muirhead, "A safe and effective low pressure tourniquet." Journal of Bone and Joint Surgery, Vol. 68-B, 1986, pp. 625-628.

J. A. Shaw, W. W. Demuth, and A. W. Gillespy, "Guidelines for the use of digital tourniquets based on physiological pressure measurements." The Journal of Bone and Joint Surgery, Vol. 67-A, 1985, pp. 1086-1090.

S. E. Grice et al., "Intravenous regional anesthesia: Evaluation and prevention of leakage under the tourniquet." Anesthesiology, Vol. 65, pp. 316-320, 1986.

SUMMARY OF THE INVENTION

The invention is directed toward a tourniquet comprising: an occlusive band for encircling a limb of a subject and for applying pressure to the limb wherein an inner surface of at the band faces the limb; and applied pressure sensing means located at a predetermined position on the inner surface of the band for producing an indication of the pressure applied by the band to the limb near the predetermined location. The applied pressure sensing means may produce an applied pressure signal representative of the pressure applied by the band to the limb near the predetermined location, the occlusive band may be responsive to a variable pressure control signal, and pressure-regulating means responsive to the applied pressure signal may be included for producing a pressure control signal to maintain the pressure applied to the limb near a predetermined reference pressure.

The applied pressure sensing means may be comprised of: a first flexible layer carrying a first electrical contact; a second flexible layer carrying a second electrical contact and cooperating with the first flexible layer to define a flexible pressurizable chamber wherein the first and second electrical contacts are touching, near the predetermined location when the chamber is not pressurized; and pressure estimation means for selectable pressurizing the chamber, and for producing an applied pressure signal representative of the lowest pressure at which the first and second electrical contacts are separated. The applied pressure sensing means may be comprised of material having a degree of flexibility and physical dimensions selected so that the sensing means conforms closely to the surface of the occlusive band and does not substantially displace the surface of the limb away from the band surface.

The invention is also directed toward a tourniquet comprising: an occlusive band for encircling a limb of a subject and for applying pressure to the limb, wherein an inner surface of the band faces the limb; and applied pressure sensing means located at a plurality of predetermined positions on the inner surface of the band for producing an indication of the pressures applied by the band to the limb near each of the predetermined locations. The applied pressure sensing means may produce a plurality of applied pressure signals representative of the pressures applied by the band to the limb near each of the predetermined locations, the occlusive band may be responsive to a variable pressure control signal, and pressure-regulating means responsive to at least one of the applied pressure signals may be included for producing a pressure control signal to maintain the pressure applied to the limb near at least one predetermined location near a predetermined reference pressure.

The invention is also directed toward apparatus for controlling the pressure applied to a body tissue by pressure-applying means near a predetermined location relative to the pressure-applying means, comprising: pressure-applying means responsive to a pressure control signal for applying pressure to a tissue; transducing means comprised of: a first flexible layer carrying a first electrical contact, a second flexible layer carrying a second electrical contact and cooperating with the first flexible layer to define a flexible pressurizable chamber interposed between the tissue and the pressure-applying means, wherein the first and second electrical contacts are touching near a predetermined location relative to the pressure-applying means when the chamber is not pressurized; and pressure estimation means for selectable pressurizing the chamber, and for producing an applied pressure signal representative of the lowest pressure at which the first and second electrical contacts are separated; and pressure-regulating means responsive to the applied pressure signal for producing a pressure control signal to maintain the pressure applied to the tissue by the pressure-applying means near a predetermined reference pressure.

Brief Description of the Drawings

A specific embodiment of this invention has been chosen for purposes of illustration and description wherein.

Description of the Specific Embodiment

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 2:
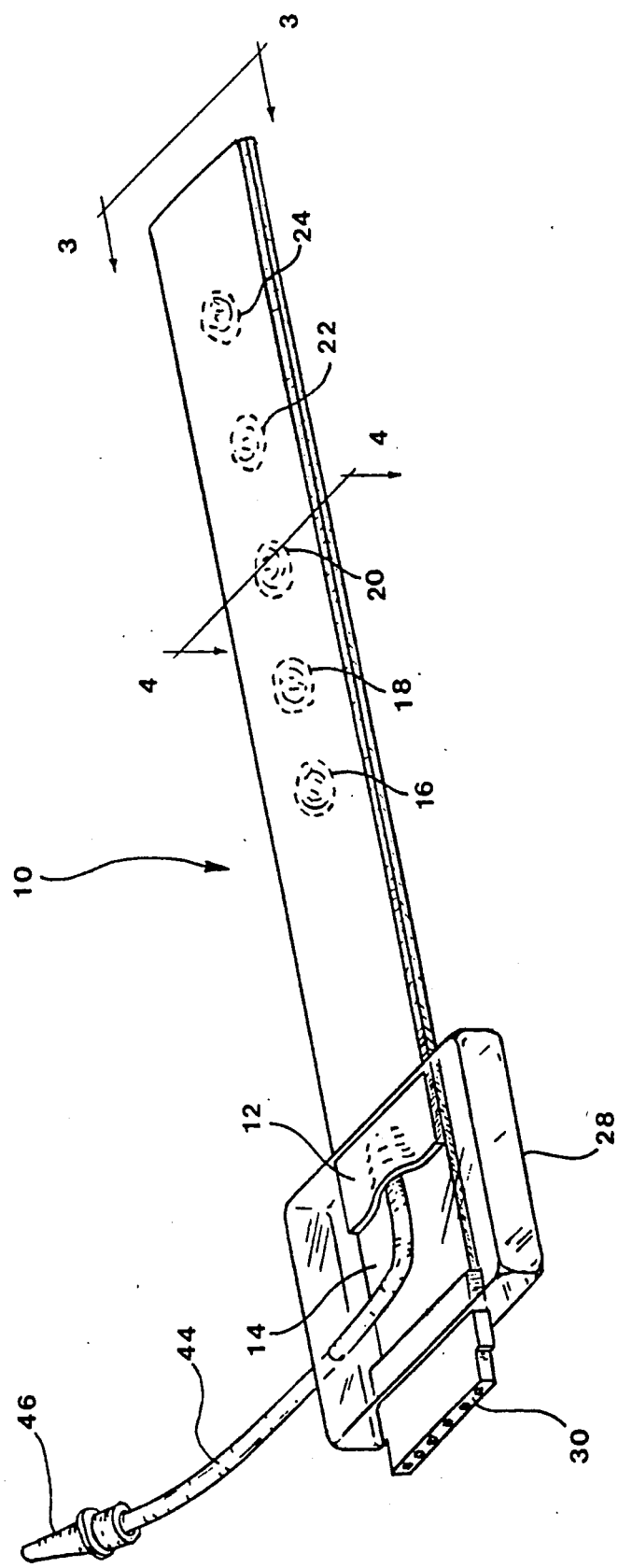
FIG. 2 is a perspective view of the transducer of FIG. 1.

The biomedical pressure transducer 10 portion of the tourniquet of this invention, as can be seen in FIG. 2, includes upper contact support layer 12 and lower contact support layer 14 which have a similar, generally rectangular shape and which are made of flexible, inextensible transparent polyester known as Mylar (DuPont trademark) that is approximately 5 mils thick.

Figure 3:
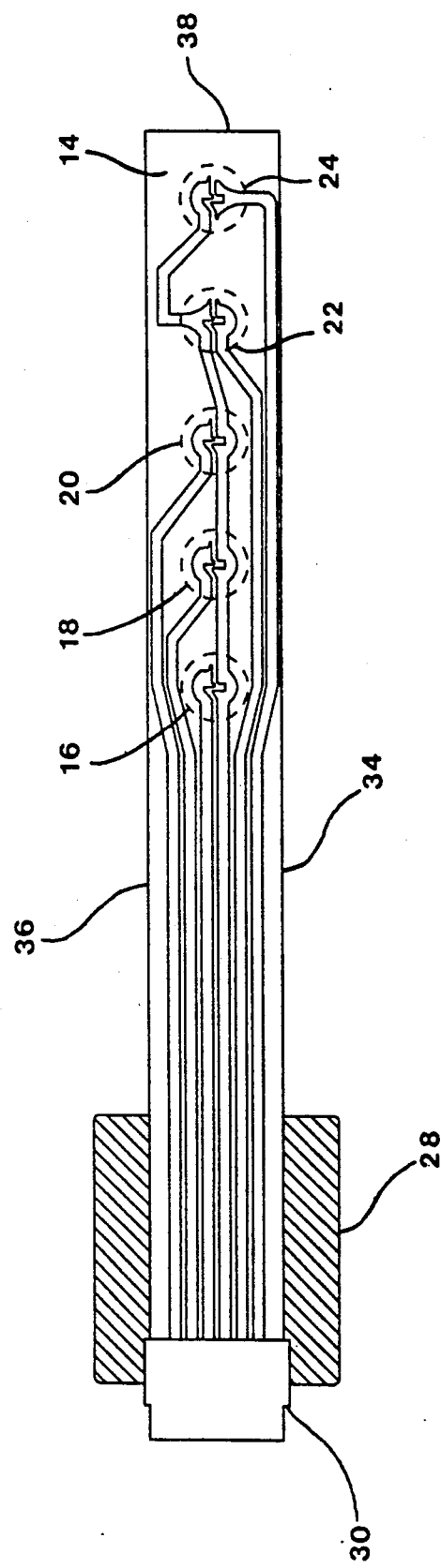
FIG. 3 is a sectional view taken along line 3—3 of FIG. 2.
Figure 4B:
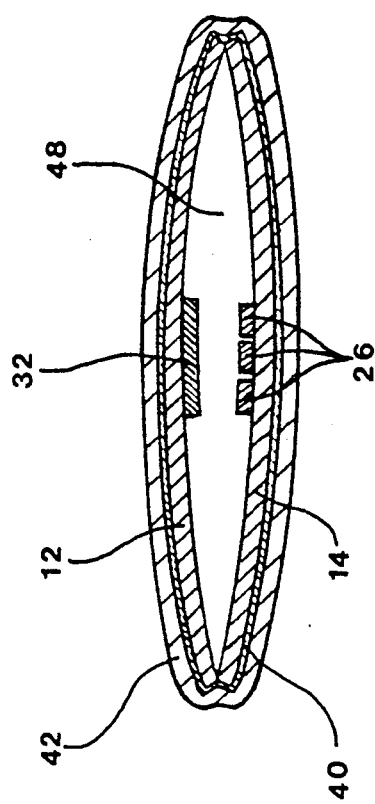
FIGS. 4A and 4B are sectional views taken along line 4—4 of FIG. 2 while the transducer is not pressurized, and while the transducer is pressurized, respectively.
Figure 4A:
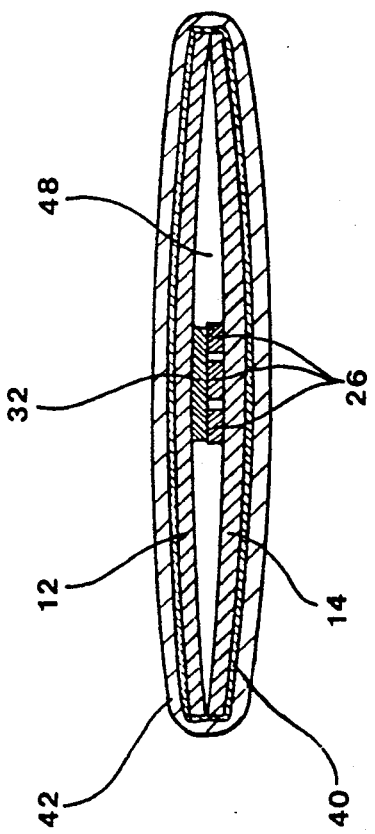

FIG. 3 shows lower contact support layer 14 which has five circular switch contact areas 16, 18, 20, 22 and 24. In each switch contact area on lower contact support layer 14 are adjacent switch contacts 26 formed of a pattern of conductive silver ink (Electrodag 415SS, manufactured by Acheson Colloids, Port Huron, Mich.) having a thickness of approximately 0.4 mils and connected to leads of similar thickness formed of conductive silver ink which go through connecting block 28 to electrical connector 30. On upper contact support layer 12 directly over each of switch contact areas 16, 18, 20, 22 and 24 of lower contact support layer 14 is an upper switch contact 32 formed of a pattern of conductive silver ink having a thickness of about 0.4 mils and designed to short and form an electrical connection between adjacent switch contacts 26 on lower contact support layer 14 when the two layers are pressed together, as shown in FIG. 4A. Thus adjacent switch contacts 26 at each of the five switch contact areas 16 to 24 on lower contact support layer 14, together with the shorting upper switch contact 32 on upper contact support layer 12, form five switches located within switch contact areas 16, 18, 20, 22 and 24 near the longitudinal axis of layers 12 and 14. The five switches formed in this manner are normally closed, i.e. upper switch contact 32 is touching and shorting electrically adjacent switch contacts 26, when the upper and lower contact support layers 12 and 14 are pressed together. For the specific embodiment, upper contact support layer 12, lower contact support layer 14 and electrical connector 30 were conveniently obtained by disassembling and modifying components of a commercially available membrane switch (Brady Xymox 1×5 Membrane Switch Unit manufactured by W. H. Brady Co., Milwaukee, Wis.).

Upper and lower contact support layers 12 and 14 were sealed together along edges 34 and 36 from approximately 1 cm below electrical connector 30 to distal end 38 by first wrapping flexible, transparent adhesive tape 40 (Highland Type "371" Tape manufactured by the 3M Company, St. Paul, Minn.) around the outer surfaces of upper and lower contact support layers 12 and 14 as shown in FIG. 4A. Care was taken to seal tape 40 thoroughly to itself at distal end 38, and to assure that the entire outer surfaces of upper and lower contact support layers 12 and 14 adhered firmly to tape 40. The taped portion of layers 12 and 14 was then repeatedly dipped in a rubber coating liquid (Plasti Dip Flexible Air Dry Rubber Coating manufactured by PDI Inc., St. Paul, Minn.) which dried in air to form a thin, flexible, transparent sheath 42 which was fluid-tight and which enabled the taped and sheathed portion of transducer 10 to withstand repeated pressurization to more than 600 mmHg without leaking or rupturing.

After sheath 42 was applied, the sheathed layers were positioned in relation to connecting block 28 as shown in FIG. 2. A short length of clear vinyl tubing 44 with male Luer-lock fitting 46 attached at one end was inserted through a side of connecting block 28 and then between upper and lower contact support layers 12 and 14, as shown in FIG. 2. After tubing 44 was inserted, connecting block 28 was filled with a clear epoxy resin which, when it cured, formed a strong, fluid-tight seal at the proximal end of transducer 10, thus establishing a pressurizable chamber 48 shown in FIGS. 4A and 4B. Pressurizable chamber 48 extends along substantially all of the length of sheathed contact support layers 12 and 14 and surrounds all switch contact areas 16 to 24 due to the non-zero thickness of the switch contacts and leads, as shown in FIG. 4A, and can be pressurized via the conduit means comprised of tubing 44 and Luer-lock fitting 46.

Figure 1:
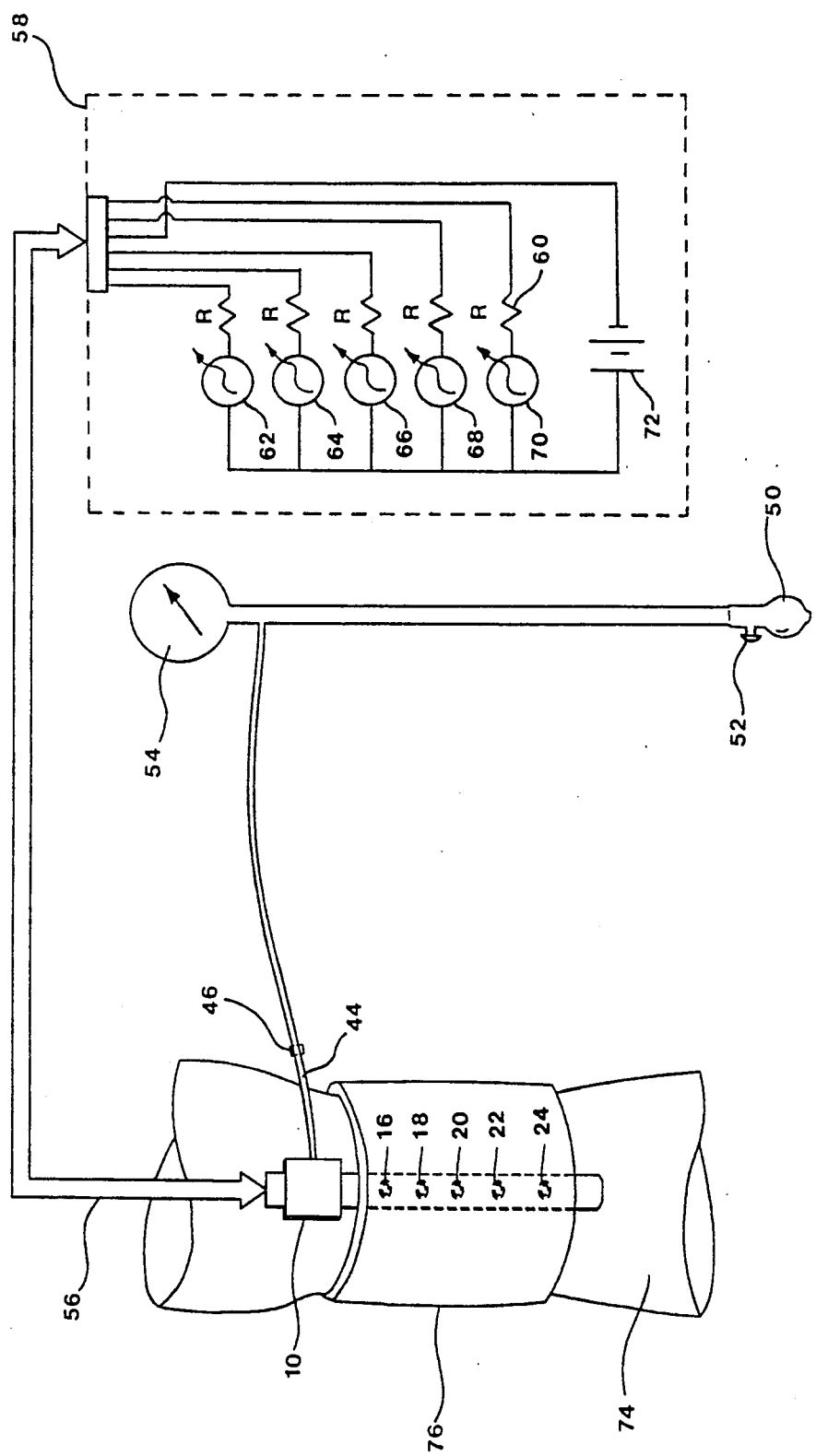
FIG. 1 is a schematic diagram depicting the biomedical pressure transducer portion of the tourniquet of this invention.

As shown in FIG. 1, in order to use transducer 10, fitting 46 is first coupled to pressurizing means 50, depressurizing means 52, and pressure-indicating means 54. In the specific embodiment, pressurizing means 50 was a hand bulb from an aneroid sphygmomanometer set, depressurizing means 52 was a manual bleed valve attached to the hand bulb, and pressure-indicating means 54 was an aneroid pressure gage. Although pressurized air is described in the specific embodiment, any pressurized fluid that is non-conductive electrically and non-reactive chemically may be employed. Transducer 10 is connected via electrical cable 56 to electrical circuitry 58, as shown in FIG. 1. Electrical circuitry 58, which includes five similar current-limiting resistors 60, five light-emitting diodes 62, 64, 66, 68 and 70, and battery 72, connects the switch contacts in each of the five switch contact areas 16 through 24 to a corresponding light-emitting diode so that light is emitted when the corresponding switch contacts are touching, i.e. when the corresponding switch is in its normally closed state.

In the simplest tourniquet of the invention illustrated in FIG. 1, transducer 10 is attached by techniques such as physically or chemically bonding it to the inner surface of occlusive band 76 which encircles and applies pressure to limb 74, in order to predetermine the relative locations of switch contact areas 16 to 24 with respect to occlusive band 76. Transducer 10 is designed to be sufficiently thin, narrow and flexible so that it does not displace substantially the tissue of limb 74 from its normal location in relation to occlusive band 76, and is designed to be sufficiently long to extend above and below the edges of occlusive band 76 and to have switch contact areas 16, 18, 20, 22, and 24 positioned at proximal, mid-proximal, middle, mid-distal, and distal locations, respectively, in relation to occlusive band 76. While the pressurizable chamber 48 of transducer 10 is not pressurized, all switch contacts are touching i.e. all switches are in their normally closed state, and all light-emitting diodes 62 to 70 emit light. Pressurizable chamber 48 of transducer 10 is then gradually pressurized by an operator activating pressurizing means 50, who observes the status of light-emitting diodes 62 through 70 and at the same time observes the pressure indicated by pressure-indicating means 54. The lowest pressure at which each light-emitting diode stops emitting light is recorded: each pressure thus recorded is an estimate of the pressure applied by occlusive band 76 in a normal direction onto the surface of limb 74 beneath the corresponding switch contact area. Once pressurizable chamber 48 of transducer 10 has been pressurized sufficiently to extinguish all light-emitting diodes, the operator may use depressurizing means 52 to gradually depressurize chamber 48 of transducer 10 and record the highest pressure at which each of the light-emitting diodes begins emitting light, thus providing a second estimate of the pressure applied in a normal direction beneath the corresponding switch contact area and also providing (by comparison with the corresponding estimate obtained previously while pressure was increasing) an estimate of any inherent hysteresis that may exist in transducer 10 and in the other elements of the pressure estimation system. The set of pressure estimates obtained by manually pressurizing and depressurizing pressurizable chamber 48 of transducer 10 as described above is of intrinsic significance in many clinical applications.

Figure 5:
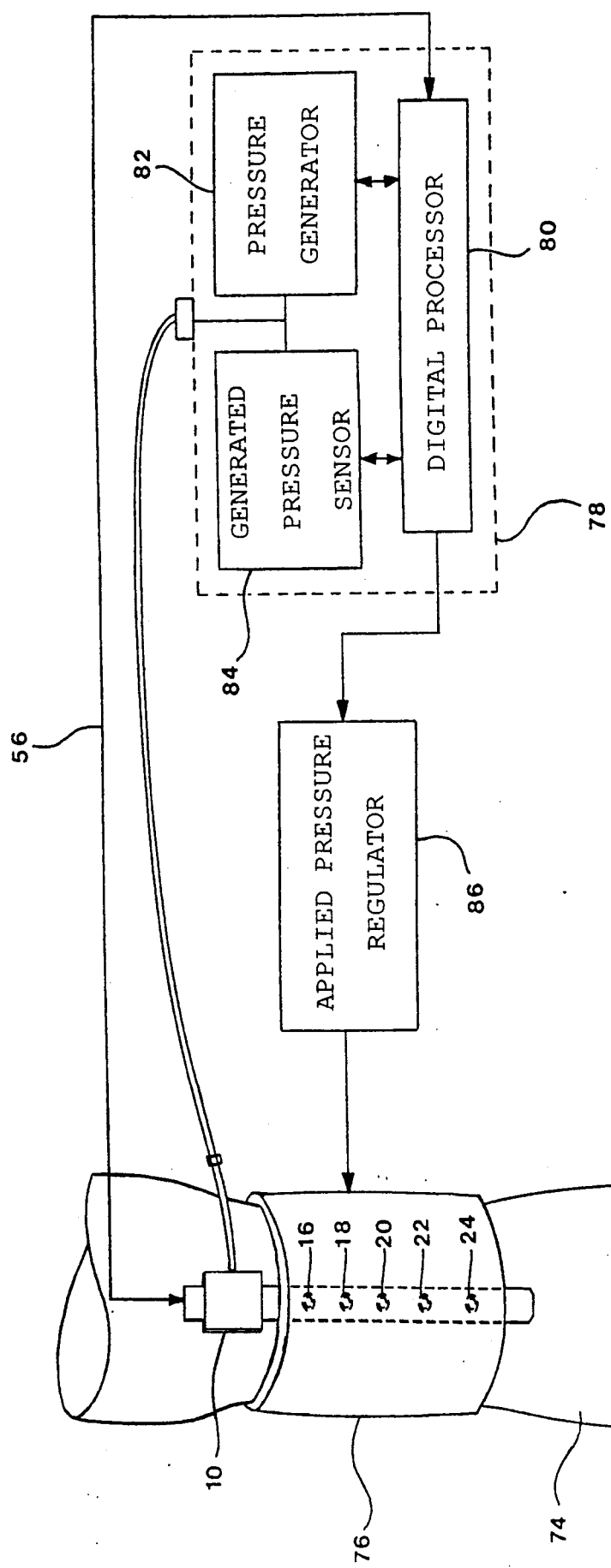
FIG. 5 is a block diagram of a tourniquet for regulating a pressure applied to a limb, showing the transducer connected to electrical circuitry and apparatus for controlling the pressure applied by the occlusive band of the invention to the limb near a predetermined location relative to the band.

FIG. 5 shows the tourniquet of the invention in a configuration which automatically maintains the pressure applied to the surface of tissue beneath a selected switch contact area near a predetermined reference pressure. As shown in FIG. 5, transducer 10 is attached to automated transducer controller 78. Automated transducer controller 78 includes digital processor 80 for selectable pressurizing and depressurizing pressurizable chamber 48 of transducer 10 by controlling pressure generator 82, comprised of an electric pump and electrical pressure-relief valve. Digital processor 80 estimates the pressures applied to the surface of tissue beneath switch contact areas by reading the level of the signal produced by generated pressure sensor 84 as the switches at switch contact areas 16 to 24, which are monitored via electrical cable 56, change states during predetermined pressurization and depressurization cycles. Digital processor 80 produces an output signal representative of the pressures applied at the switch contact areas for controlling applied pressure regulator 86 in order to maintain the pressure applied to an area of the surface of limb 74 beneath a selected switch contact area near a predetermined reference pressure. This pressure regulation can be conveniently achieved in practice by, for example, interfacing the output signal of digital processor 80 to an automated tourniquet system such as one of the ATS 1500 or ATS 500 automatic tourniquet systems manufactured by Aspen Laboratories of Englewood, Colo., which then functions as applied pressure regulator 86.

Figure 6:
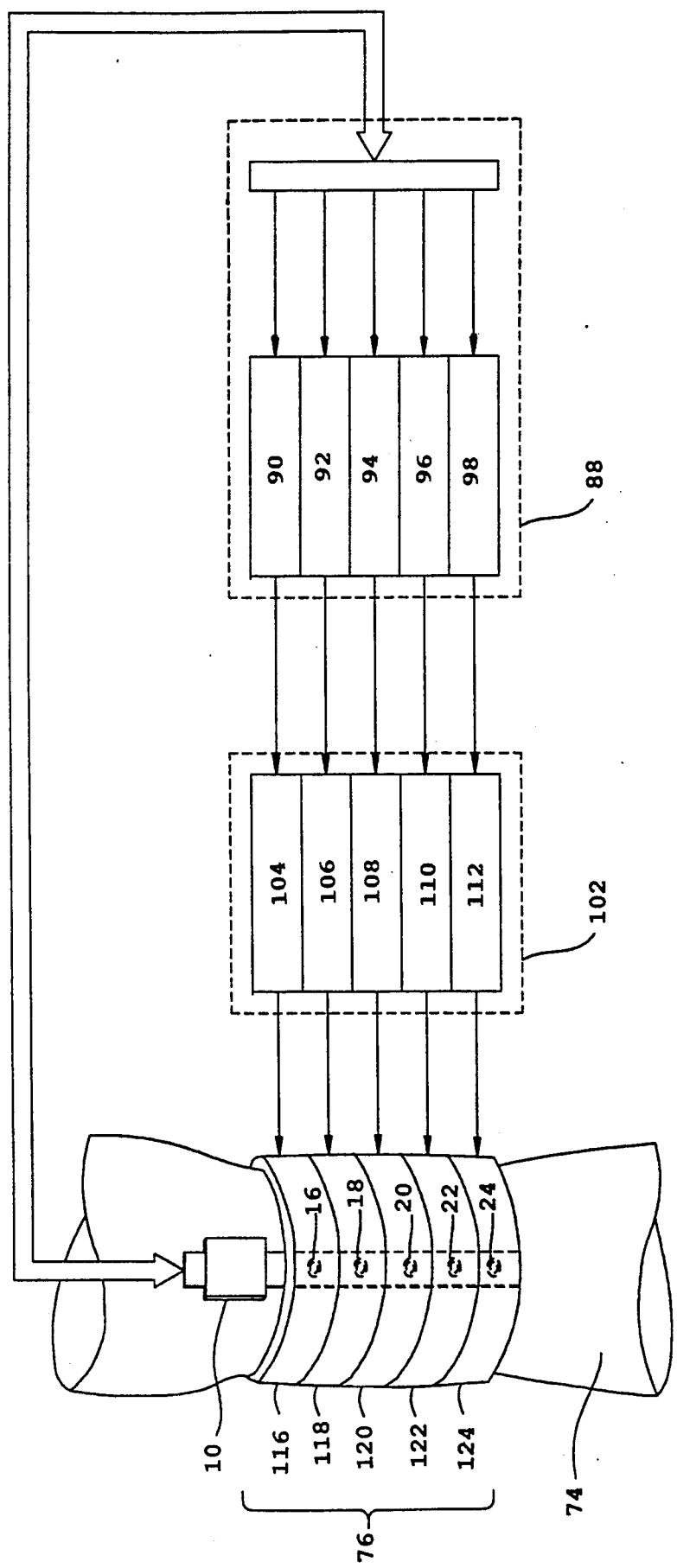
FIG. 6 is a block diagram of a tourniquet for regulating more than one pressure applied to a limb, showing an occlusive band having five separately controllable segments with the transducer connected to electrical circuitry and apparatus for separately regulating the pressure applied by each of the five segments of the occlusive band to the limb near five predetermined locations relative to the band.

FIG. 6 shows the tourniquet of the invention in a configuration which separately and simultaneously regulates multiple pressures actually applied to the limb. Occlusive band 76 shown in FIG. 6 is comprised of five separately controllable segments 116, 118, 120, 122 and 124 located above switch contact areas 16, 18, 20, 22 and 24 respectively. Transducer interface 88 shown in FIG. 6 is connected to transducer 10 and is comprised of five elements 90, 92, 94, 96 and 98 which produce five signals representative of the pressures applied by occlusive band segments 116, 188, 120, 122 and 124 to the limb near switch contact areas 16, 18, 20, 22 and 24 respectively. Pressure controller 102 is comprised of five separate pressure controlling elements 104, 106, 108, 110 and 112, is responsive to the five signals from transducer interface 88 and maintains the pressures applied to the surface of limb 74 beneath each of the five switch contact areas 16, 18, 20, 22 and 24 near five predetermined reference pressures. In this manner, clinically desired pressure distributions and gradients can be achieved along the limb longitudinally.

As will be apparent to those skilled in the art, in the light of the foregoing disclosure many alterations and modifications are possible in the practice of this invention without departing from the scope or spirit thereof. For example, the transducer portion of the invention may be implemented non-pneumatically by employing a flexible material in which a parameter such as the electrical resistance changes in response to variations in applied pressure, e.g. force sensing resistors manufactured by Interlink Electronics (Santa Barbara Calif.). Also, the occlusive band of the invention having one or more separately controllable segments may be implemented nonpneumatically. The construction of the transducer and occlusive band portions of the invention may be completely integrated. An another example of possible alterations and modifications in the practice of this invention, the number and shape of separately controllable segments of the occlusive band, as well as the number, size and locations of the pressure-sensing areas of the transducer can be changed to meet clinical requirements. In this manner, desired pressure gradients and desired pressure distributions can be achieved either along the limb longitudinally or around the limb circumferentially.

I claim:

1. Apparatus for controlling the pressure applied to a body tissue by pressure-applying means near a predetermined location relative to the pressure-applying means, comprising:

pressure-applying means responsive to a pressure control signal for applying pressure to a tissue;

transducing means comprised of:

a first flexible layer carrying a first electrical contact;

a second flexible layer carrying a second electrical contact and cooperating with the first flexible layer to define a flexible pressurizable chamber interposed between the tissue and the pressure-applying means, wherein the first and second electrical contacts are touching near a predetermined location relative to the pressure-applying means when the chamber is not pressurized; and pressure estimation means for selectable pressurizing the chamber, and for producing an applied pressure signal representative of the lowest pressure at which the first and second electrical contacts are separated; and pressure-regulating means responsive to the applied pressure signal for producing a pressure control signal to maintain the pressure applied to the tissue by the pressure-applying means near a predetermined reference pressure.

2. A tourniquet comprising:

an occlusive band responsive to a variable pressure control signal for encircling a limb of a subject and for applying pressures to the limb wherein an inner surface of at the band faces the limb;

applied pressure sensing means located at a predetermined location on the inner surface of the band for producing an applied pressure signal representative of the pressure applied by the band to the limb near the predetermined location wherein the applied pressure sensing means is comprised of:

a first flexible layer carrying a first electrical contact, a second flexible layer carrying a second electrical contact and cooperating with the first flexible layer to define a flexible pressurizable chamber wherein the first and second electrical contacts are touching, near the predetermined location when the chamber is not pressurized, and pressure estimation means for selectably pressurizing the chamber, and for producing an applied pressure signal representative of the lowest pressure at which the first and second electrical contacts are separated; and pressure-regulating means responsive to the applied pressure signal for producing a pressure control signal to maintain the pressure applied to the limb near a predetermined reference pressure.

3. A tourniquet comprising:

an occlusive band responsive to a variable pressure control signal for encircling a limb of a subject and for applying pressures to the limb, wherein an inner surface of the band faces the limb;

applied pressure sensing means located at a plurality of predetermined locations on the inner surface of the band for producing a plurality of applied pressure signals representative of the pressures applied by the band to the limb near each of the predetermined locations wherein the applied pressure sensing means is comprised of:

a first flexible layer carrying a plurality of first electrical contacts, a second flexible layer carrying a plurality of electrical contacts and cooperating with the first flexible layer to define a flexible pressurizable chamber wherein pairs of first and second electrical contacts are touching, near the plurality of predetermined locations when the chamber is not pressurized, and pressure estimation means for selectably pressurizing the chamber, and for producing a plurality of applied pressure signals representative of the lowest pressures at which each pair of electrical contacts is separated; and pressure-regulating means responsive to at least one of the applied pressure signals for producing a pressure control signal to maintain the pressure applied to the limb near at least one predetermined location near a predetermined reference pressure.

4. A tourniquet comprising:

an occlusive band responsive to a variable pressure control signal for encircling a limb of a subject and for applying pressures to the limb wherein an inner surface of at the band faces the limb;

applied pressure sensing means located at a predetermined location on the inner surface of the band for producing an applied pressure signal representative of the pressure applied by the band to the limb near the predetermined location wherein the applied pressure sensing means is comprised of:

a first flexible layer carrying a first electrical contact, a second flexible layer carrying a second electrical contact and cooperating with the first flexible layer to define a flexible pressurizable chamber wherein the first and second electrical contacts are touching, near the predetermined location when the chamber is not pressurized, and pressure estimation means for selectably depressurizing the chamber from a level at which the contacts are separated, and for producing an applied pressure signal representative of the highest pressure at which the contacts touch; and pressure-regulating means responsive to the applied pressure signal for producing a pressure control signal to maintain the pressure applied to the limb near a predetermined reference pressure.

5. A tourniquet comprising:

an occlusive band responsive to a variable pressure control signal for encircling a limb of a subject and for applying pressures to the limb, wherein an inner surface of the band faces the limb;

applied pressure sensing means located at a plurality of predetermined locations on the inner surface of the band for producing a plurality of applied pressure signals representative of the pressures applied by the band to the limb near each of the predetermined locations wherein the applied pressure sensing means is comprised of:

a first flexible layer carrying a plurality of first electrical contacts, a second flexible layer carrying a plurality of electrical contacts and cooperating with the first flexible layer to define a flexible pressurizable chamber wherein pairs of first and second electrical contacts are touching, near the plurality of predetermined locations when the chamber is not pressurized, and pressure estimation means for selectably depressurizing the chamber from a level at which all pairs of contacts are separated, and for producing a plurality of applied pressure signals representative of the highest pressures at which each pair of contacts touch; and pressure-regulating means responsive to at least one of the applied pressure signals for producing a pressure control signal to maintain the pressure applied to the limb near at least one predetermined location near a predetermined reference pressure.

6. A tourniquet for occluding blood flow into a limb over a time period suitably long for the performance of a surgical procedure, comprising:

an occlusive band for encircling a limb of a subject and for applying pressure to the encircled limb to occlude blood flow into the limb distal to the band wherein an inner surface of the band faces the limb; and applied pressure sensing means located at a predetermined location fixed relative to and in contact with the inner surface of the band for producing an indication of the pressure applied by the band to the surface of the limb in a normal direction at the predetermined location.

7. A tourniquet as defined in claim 6, wherein the applied pressure sensing means produces an applied pressure signal representative of the pressure applied by the band to the limb near the predetermined location, wherein the occlusive band is responsive to a variable pressure control signal, and including pressure-regulating means responsive to the applied pressure signal for producing a pressure control signal to maintain the pressure applied to the limb near a predetermined reference pressure.

8. A tourniquet for establishing a bloodless surgical field to facilitate limb surgery, comprising:

a cuff, attachable to a limb for applying pressure to the limb to occlude blood flow into the limb distal to the band, the cuff having an inner surface positionable in contact with the limb; and a plurality of sensors fastened to the inner surface of the cuff for detecting the pressure applied by the cuff to the surface of the limb at a plurality of locations in a direction normal to the cuff at each of the locations.

9. A tourniquet as defined in claim 8 wherein the sensors produce a plurality of applied pressure signals representative of the pressure applied by the cuff to the limb near each of the locations, wherein the cuff is responsive to a variable pressure control signal, and including pressure-regulating means responsive to at least one of the applied pressure signals for producing a pressure control signal to maintain the pressure applied to the limb near at least one location near a predetermined reference pressure.

10. A tourniquet for establishing a bloodless surgical field to facilitate limb surgery comprising:

an occlusive band for encircling a limb of a subject and for simultaneously applying a plurality of pressures to the encircled limb to occlude blood flow into the limb distal to the band, wherein an inner surface of the band faces the limb;

applied pressure sensing means for producing an indication of the pressure applied by the band to the surface of the limb in a direction normal to the inner surface of the band at a predetermined location on the inner surface of the band; and fixing means for fixing the location of the applied pressure sensing means relative to the predetermined location on the inner surface of the band over a time period suitably long for the performance of a surgical procedure.

11. A tourniquet for establishing a bloodless surgical field to facilitate limb surgery, comprising:

an occlusive band for encircling a limb of a subject;

pressure means for simultaneously applying a plurality of selected pressures to the surface of the encircled limb to occlude blood flow into the limb distal to the band; and pressure sensing means for producing an indication of the pressure applied by the pressure means to the surface of the limb near any of a plurality of locations near the band.

* * * * *